United States Patent
Fouillet et al.

(10) Patent No.: US 6,395,557 B1
(45) Date of Patent: May 28, 2002

(54) METHOD FOR DETERMINING AN ANALYTE PRESENT IN A SOLUTION

(75) Inventors: Yves Fouillet, Voreppe; Alain Theretz, Ecully; Agnès Perrin, Lyons, all of (FR)

(73) Assignees: Commissariat a L'Energie Atomique, Paris (FR); Biomerieux SA, Marcy L'Etoile (FR)

( * ) Notice: Subject to any disclaimer, the term of this patent is extended or adjusted under 35 U.S.C. 154(b) by 0 days.

(21) Appl. No.: 09/505,156

(22) Filed: Feb. 15, 2000

(30) Foreign Application Priority Data

Feb. 24, 1999 (FR) .............................. 99 02288

(51) Int. Cl.$^7$ ................................. G01N 7/00
(52) U.S. Cl. .............. 436/148; 435/7.1; 435/286.5; 435/287.2; 422/68.1; 422/82.13; 436/52; 436/518; 73/61.64; 73/61.67
(58) Field of Search ............. 422/58, 68.1, 81, 422/82, 82.13, 97, 101, 102, 103, 104, 112; 73/61.62, 61.64, 61.67, 61.78; 435/4, 7.1; 436/50, 52, 514, 148, 518, 531, 535, 146

(56) References Cited

U.S. PATENT DOCUMENTS

| | | | |
|---|---|---|---|
| 4,964,847 A | 10/1990 | Prince ........................ | 604/4 |
| 6,007,999 A | * 12/1999 | Clark et al. .................. | 435/7.1 |
| 6,171,865 B1 | * 1/2001 | Weigl et al. .................. | 436/52 |
| 6,200,814 B1 | * 3/2001 | Malmqvist et al. ........... | 436/52 |
| 6,221,677 B1 | * 4/2001 | Wu et al. ..................... | 436/518 |

FOREIGN PATENT DOCUMENTS

| | | |
|---|---|---|
| FR | 2727648 | 6/1996 |
| FR | 2758884 | 7/1998 |

* cited by examiner

*Primary Examiner*—Long V. Le
*Assistant Examiner*—Gary W. Counts
(74) *Attorney, Agent, or Firm*—Burns, Doane Swecker & Mathis LLP

(57) ABSTRACT

The invention relates to a method for determining an analyte in a solution. This method includes the following steps:

a) fixing and immobilizing said analyte, for example via the presence of a ligand L, on the inner surface of a conduit (3) having a reduced cross section over all or part (9) of it, and b) determining the variation in load loss of a fluid circulating inside the conduit, due to the analyte P which has been fixed and immobilized at least in the reduced cross section part (9) of said conduit during step a).

17 Claims, 4 Drawing Sheets

METHOD FOR DETERMINING AN ANALYTE PRESENT IN A SOLUTION

TECHNICAL FIELD

The subject matter of the present invention is a method for determining an analyte present in a solution. More precisely, it relates to a method with which it is possible to detect and/or quantify this analyte. The analyte may be a chemical or biological entity.

Therefore, the present invention finds numerous applications in the area of chemical or biological analysis, for example for the determination of antigens, antibodies, DNA or RNA sequences, bacteria, viruses, bacterial fragments, etc.

PRIOR ART

Numerous systems for chemical or biological analyses are based on the reaction of the analyte to be determined with a suitable compound to form a reaction product, which must subsequently be detected and/or quantified in order to determine the presence and concentration of this analyte. Generally, this detection is made via labellers such as radioactive or luminescent tracers, enzymes or others which may be carried by the added compound added to react with the analyte to be detected. The use of such tracers assumes the use of specific apparatus to ensure the detection and/or quantification of the analyte.

Other detection and quantification methods such as topographic methods for example using atomic force microscopy (AFM), magnetic methods, electric methods for example by measuring capacity variation, and optic methods may also be used as described in FR-A-2 758 884 (1).

These methods, however, also have the disadvantage of requiring specific apparatus which can at times be costly.

The present invention sets out precisely to provide a method of determining an analyte which avoids the use of such apparatus and ensures the detection and/or quantification of the analyte using very conventional components at affordable price.

DESCRIPTION OF THE DISCLOSURE

According to the invention, the method for determining an analyte in a solution comprises the following steps:
  a) fixing and immobilizing said analyte on the inner surface of a conduit having a reduced cross section over all or part of it, and
  b) determining the variation in load loss of a fluid circulating inside the conduit, due to the analyte which has been fixed and immobilized at least in the reduced cross section part of said conduit during step a).

The method of the invention is therefore based on the use of a conduit having a suitable cross section over all or part of it, in which, during step a), the analyte to be determined is fixed and immobilized.

The fixing and immobilization of the analyte is made at least over all or part of the reduced cross section of the conduit, but they may also be conducted over the entire conduit.

This fixing and immobilization may be made either by contacting the solution with the inner surface of the conduit (for example by dipping) or by circulating the solution in the conduit, this circulation possibly entailing at least one sequential stop.

During the subsequent step b), the variation in load loss of a fluid circulating in the conduit is determined, such variation resulting from fixation of the analyte and being related to the quantity of analyte fixed.

This quantification of the analyte may be conducted using pre-set plots or curves, or by experimentation, or by simulation on the basis of known geometric data on the conduit and on the analytes used (size and quantity). Therefore, the value of the load loss is related to the quantity of analyte immobilized in the conduit and/or the size of this analyte.

Through experimentation, it is possible to cross-refer the measurement obtained in the method of the invention to previously made measurements to calibrate the performance of the conduit.

With both these methods it is possible to plot graphs showing the relationship between load loss and the quantity of immobilized analyte. Therefore, via simple measurement of load loss, it is possible to quantify the level of analyte immobilized in the conduit during step a) of the method of the invention.

According to the invention, it is possible to determine the variation in load loss by measuring the difference in pressure, at constant flow rate between two points located either side of the reduced cross section of the conduit, of a fluid circulating in the conduit before carrying out step a) and after conducting step a) of the method, or else the difference in flow rate at constant pressure before and after step a).

The fluid used for this determination may be all or part of the initial solution (in this case, step a) and step b) are simultaneous or successive) or a different liquid to this solution.

In the prior art, measurement of load loss in a conduit with a circulating fluid was used to determine certain characteristics of the fluid, its viscosity for example, and consequently its content of a particular product able to modify its viscosity. In document U.S. Pat. No. 4,964,847 [2] for example, this measurement is used to estimate packed cell volumes in blood.

This type of determination method is different from the method of the invention in which detection and quantification of the analyte require its immobilization on the wall of a conduit having a suitable shape and having, in addition, the property of being able to fix the analyte to be determined.

This latter property may be conferred upon the conduit by fixing on its wall a ligand that is able to bind with the analyte.

In this case, the determination of the analyte involves a recognition reaction between the analyte and the ligand with formation of an analyte-ligand complex immobilized in the conduit.

In this embodiment of the method of the invention, prior to step a), the wall of the reduced cross section is coated over all or part with at least one ligand able to fix itself to the analyte.

In this case, the presence of the ligand can be detected by determining the variation in load loss through measurement of the difference in pressure at constant flow rate, or the difference in flow rate at constant pressure, between two points located either side of the reduced cross section of the conduit, of a fluid circulating inside the conduit before and after making the ligand coating.

According to one variant of embodiment of the invention, when the size of analyte to be determined, or of the complex formed through reaction of this analyte with a ligand, is too small to generate sufficient load loss in the reduced cross section part of the conduit, a physical or chemical reaction of the analyte is additionally performed with a support material to form an analyte-support conjugate of greater size than the analyte, this reaction taking place either when said analyte is free in the solution, before step a), or when the analyte is already fixed directly or indirectly onto the inner wall of the reduced cross section part of the conduit after step a) to form an analyte-support conjugate.

This reaction between the analyte and the support material may be conducted before adding the solution to the conduit, or before conducting step a), or after fixing the analyte on the wall of the reduced cross section part of the conduit, that is to say after step a) but before step b).

To promote the binding of the support material with the analyte, the latter generally comprises a ligand on its surface able to bind with the analyte.

According to the invention, by "analyte" is meant any chemical or biological entity, in particular any biological entity in free form. As an illustration of analytes, the examples which may be cited are cells, organelles, viruses and bacteria, antibodies, antibody fragments, antigens, haptenes, lectines, sugars, ribonucleic and deoxyribonucelic acids, proteins, in particular A or G, hormones, hormone receptors, biotin, avidin, streptavidin and in general any molecule or macromolecule that is natural or synthetic, or analogue or even resulting from an association of at least two molecules or macromolecules of the type of those previously defined. Examples of associations of molecules or macromolecules which may be cited are the analyte-support conjugates which will be defined below.

According to the invention, by "support-material" is meant any type of biological, polymer, organic, inorganic or metallic support which may be distributed or dispersed in discrete form within a liquid medium, and most often, but not restrictively, in particle form.

Examples of support-materials of polymer type which may be cited are particles obtained by emulsion polymerization such as latex particles, or particles of greater size and grafted polymers, copolymers and polymers obtained by other means known to those skilled in the art.

Examples of support-materials of metallic type which may be cited are colloidal gold, ferromagnetic, ferrimagnetic, paramagnetic or superparamagnetic particles, whether coated or not with natural or synthetic polymers which contain iron or other metals such as cobalt, nickel or others, either alone or in alloy form, whether magnetic or not.

Examples of support-materials of inorganic type which may be cited are particles containing silica or silicon, mica, glass and/or quartz.

Examples of support-materials of biological type which may be cited are mass proteins or those of greater size than the analyte to be determined in the free state.

By "analyte-support conjugate" is meant any analyte such as previously described, immobilized on a support-material such as previously defined by any means. Immobilization of the analytes on the support-material may be made by simple adsorption or via a chemical or physical reaction able to modify the surface of the support-material and therefore enabling fixing of the analyte by covalent bonds, or by chelation or by molecular recognition via a ligand immobilized on the support-material, and by any other conventional means able to withhold an analyte well known to those skilled in the art.

By "ligand" is meant an element able, through a chemical or physical bond, to form a complex with an analyte.

Examples of ligands which may be cited are antibodies, antibody fragments, antigens, haptenes, lectines, sugars, ribonucleic acids, deoxyribonucleic acids, proteins in particular A or G, hormones, hormone receptors, biotin, avidin or streptavidin and, in general, natural or synthetic ligands and analogues of modified ligands, which may enter into competition with the ligands.

In the remaindes of this disclosure, "circulating cell" will denote any type of system comprising the conduit with its reduced cross section part, and at least two inlet and outlet pipes allowing the passage of a fluid within the conduit.

By "reduced cross-section" shall be meant a section which is generally narrower than that of the remainder of the conduit. In some cases, the entire conduit may have this reduced cross section. This portion of reduced cross section may also be called a "restriction" and, owing to its particular analyte-fixing properties, it will be called hereinafter an "active zone".

This active zone is therefore formed of the wall of the conduit on which ligands may be fixed which are able to bind with the analyte.

These ligands are fixed on the wall by any means such as by chemical reaction (covalent bonding) or physical reaction (adsorption) to modify the surface of the wall and enable fixation of the ligand.

According to the invention, the reduced cross section part of the conduit able to fix and immobilize the analyte may be of different shapes. It may in particular be round, the conduit being of cylindrical shape, or rectangular when the fluid circulation will be plane-type circulation between two parallel surfaces.

The conduit may be made in various materials, for example in materials of polymer, inorganic or metal type.

Examples of polymer materials which may be cited are polystyrene-based polymers, polyacrylates, polymethacrylates, polybutadienes, polypropylenes, or others, either alone or in the form of copolymers.

Examples of inorganic materials which may be cited include silicon oxide, silicon nitride, silicon, glass and quartz.

According to the invention, the reduced cross section part of the conduit must be dimensioned such that it is compatible with the size of the analyte to be determined.

If the conduit is of large size in relation to the size of the immobilized analyte, the presence of this analyte will not lead to a significant variation in load loss. It will therefore not be possible either to detect or to quantify the analyte.

The theories of fluid mechanics show that in general the load loss $\Delta P$ between the inlet and outlet of a portion of conduit having a reduced cross section is defined by the following equation:

$$\Delta P = KQ$$

where Q represents the volume flow of the liquid and K is a load loss coefficient related to the geometric characteristics of the conduit and the viscosity of the fluid.

According to their respective dimensions, the presence of analytes or analyte-support conjugates on the walls of the conduit causes a change in the load loss coefficient. With a conduit height close to the dimensions of the analyte or of the analyte-support conjugate, a variation in load loss coefficient is obtained which can be measured.

Therefore, to conduct the determination of the analyte under good conditions, a conduit is used whose reduced cross section part is of a size that is adapted to the size of the immobilized analyte or of the immobilized analyte-support conjugate.

Preferably, the smallest dimension $T_c$ of the reduced cross section of the conduit is such that:

$$(T_c : 3) < T_A \text{ or } e < T_c.$$

in which $T_A$ represents the size of the fixed analyte either as such or in the form of an analyte-support conjugate, on the wall of the reduced cross section part of the conduit, or e represents the thickness of the ligand.

When circulation of the fluid takes place between two parallel surfaces, $T_c$ represents the distance between the two surfaces. In respect of a cylindrical conduit, $T_c$ represents the diameter of the conduit.

The size of the analytes or analyte-support conjugates is very small since the analyte may be made up of one molecule or of one living cell; conduits of small dimensions are required, for example a few hundred nanometres or more.

Conduits having such dimensions may be obtained using microfabrication processes such as those used in microelectronics, micromechanics and, for example, using a method of the type described in FR-A-2 727 648 [3].

The method of the invention may be implemented in various manners, additionally conducting, if necessary, at least one conduit washing step between steps a) and b).

According to a first embodiment which may be used to determine analytes of sufficient volume, bacteria, viruses or bacteria fragments for example, the method entails the following steps:

1) contacting the solution containing the analyte with the active zone of the conduit to fix the analyte on this active zone,
2) washing the conduit to remove the part that has not reacted on this active zone, and
3) measuring the load loss in the conduit.

According to a second embodiment of the invention, intended to determine analytes of small size, the method entails the following steps:

1) reaction of the support-material with the analyte in the initial solution, to form the analyte-support conjugate in this solution,
2) contacting the solution with the active zone of the conduit to fix the analyte-support conjugate on this active zone,
3) washing the conduit to remove the part that has not reacted, and
4) measuring the load loss in the conduit.

According to a third embodiment of the invention, also intended to determine analytes of small size, the method entails the following steps:

1) contacting the solution containing the analyte with the active zone of the conduit to fix the analyte on this active zone,
2) washing the conduit to remove the part that has not reacted,
3) adding to the active zone of the conduit a solution containing a support-material to form the analyte-support conjugate directly on the active zone of the conduit,
4) washing the conduit to remove the support-material which has not reacted, and
5) measuring the load loss in the conduit.

Although it is preferable to use a liquid which does not contain any large molecule or biological cell to measure the load loss, it is nonetheless possible to consider using the liquids previously cited.

Therefore, according to one variant of these three embodiments, the washing step which precedes load loss measurement is omitted and this measurement is made using as liquid the solution added during the previous step, that is to say the analyte solution in the first embodiment, the analyte-support conjugate solution in the second embodiment, and the material-support solution in the third embodiment.

According to the invention, it is also possible to use the same basic principle, i.e. measurement of load loss induced by a product immobilized in a conduit, to determine the presence of a chemical or biological coating product on the inner surface of a conduit.

Therefore, a further purpose of the invention is a method to determine the presence of a chemical or biological coating on the inner surface of a conduit, which comprises the following steps:

1) placing the circulation fluid in the conduit,
2) measuring the load loss of said fluid in the conduit, and
3) determining, on the basis of measured load loss, the presence or non-presence of a coating in the conduit.

This method may be particularly useful to verify whether a ligand is in fact fixed and immobilized in the active zone of a conduit intended to determine an analyte using the method of the invention.

In this latter case, the dimensions of the conduit evidently need to be suitable to determine the load loss induced by the coating.

Preferably, the smallest dimension Tc of the conduit section is such that:

$$(T_c:3) < e\ T_c$$

where e represents the thickness of the coating.

Other characteristics and advantages of the invention will become clearer on reading the following description, which is evidently given for illustrative purposes and is non-restrictive, with reference to the appended drawings.

SHORT DESCRIPTION OF THE DRAWINGS

DETAILED DESCRIPTION OF THE EMBODIMENTS

Figure 1:
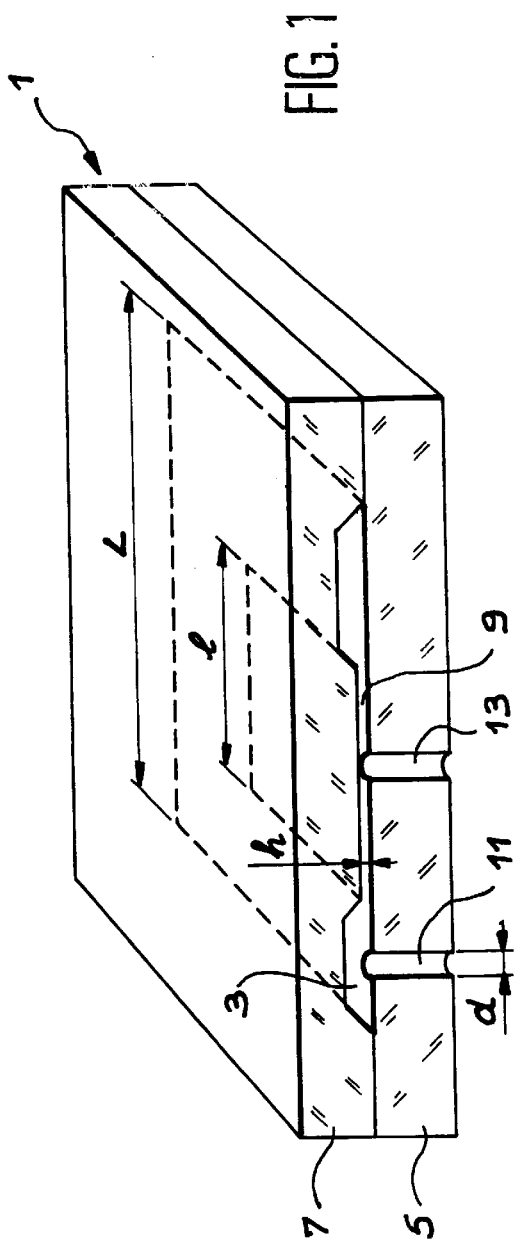
FIG. 1 shows a perspective vertical section view of a circulation cell used to implement the method of the invention.

In FIG. 1, a vertical section perspective view shows a cell to be used for circulating the solution containing the analyte to be determined.

This cell 1 contains a circulation conduit 3, between a base plate 5 and an upper plate 7 of the cell which are parallel, plates 5 and 7 being fabricated so that they form the circulation conduit 3 and the reduced cross section part 9 which is formed by a flow zone confined between the two parallel planes formed by plates 5 and 7. This flow zone 9 forms the active zone of the cell. Base plate 5 comprises two openings, inlet 11 and an outlet 13, enabling the solution to circulate in the cell passing through the confined flow zone 9.

By way of example, this cell may have the following dimensions: a height h of 1 μm in the confined flow zone 9, a length 1 of 2 mm of the confined flow zone 9, a diameter d of openings 9 and 11 of 500 μm and a length L of 5 mm of conduit 3. This cell may be made using microtechnological processes using two silicon substrates 5 and 7. In the lower substrate 5, openings 9 and 11 can be fabricated by laser etching, plasma etching or other processes. In the upper substrate 7, the confined flow zone can be delimited using etching methods.

The two substrates can then be assembled using conventional direct Si—Si sealing techniques.

Figure 2:
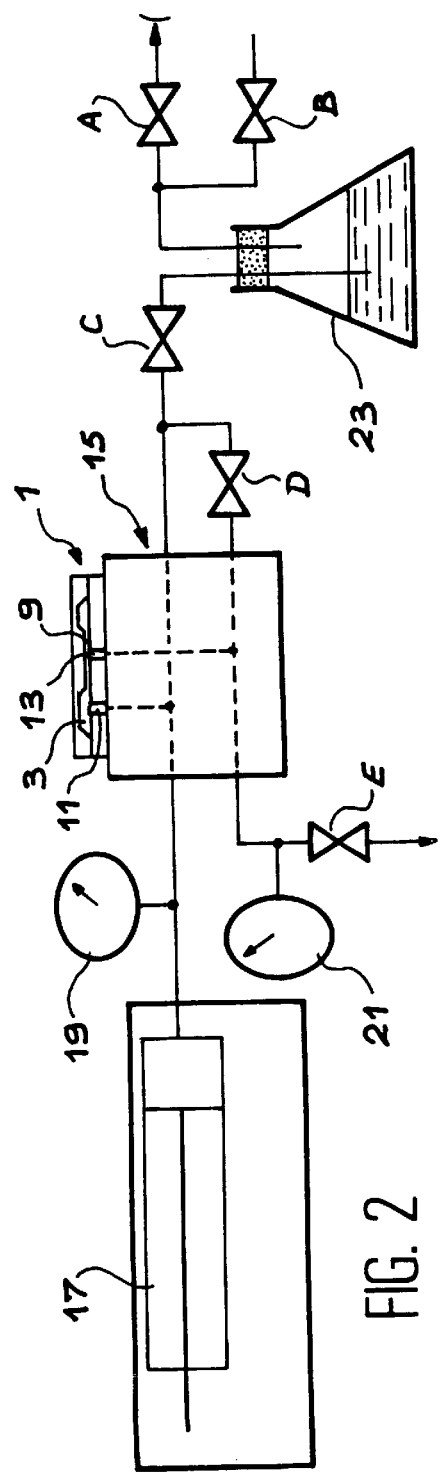
FIG. 2 is a diagram of an installation comprising the cell in FIG. 1 to implement the method of the invention and to carry out measurement of load loss.

FIG. 2 shows an assembly with which it is possible to conduct the necessary measurements and to circulate the solution in the cell of FIG. 1.

In this case, cell 1 in FIG. 1 is associated with a cell holder 15, a syringe plunger 17, a network of pipes fitted with gates A, B, C, D and E, one or two pressure sensors 19 and 21, and a bottle 23 comprising the solution to be tested, a rinsing solution or a fluid to measure load loss. The pipes are fitted with gates so that the assembly can be placed in a vacuum (gate A) or at atmospheric pressure ( gate B).

In this installation, cell 1 is cemented to cell holder 15 or fixed to the latter via a clamping system. In either case, the assembly must be perfectly well sealed. Syringe plunger 17 is used to maintain a controlled flow rate in the cell and to sample solutions from bottle 23. Measurement of load loss is conducted using the two pressure sensors 19 and 21 connected respectively to inlet 11 and outlet 13 of circulation cell 1. The second pressure sensor 21 is not necessary when the cell holder leads to a reference pressure such as atmospheric pressure.

To obtain precise measurement, the system needs to be entirely filled with liquid. The hydraulic sections in the cell are very small and gas bubbles may generate fairly substantial capillary forces which might disturb measurement of load loss. To eliminate the formation of bubbles remaining trapped in the measurement chamber, the solutions placed in circulation can be de-gased.

The same result may be achieved with the installation shown in FIG. 2 by placing the assembly in a vacuum before the first filling and by de-gasing the solutions before starting operations.

To implement the method of the invention, different solutions need to be circulated in the cell, such as analyte solutions to be determined and rinsing solutions. The shape of the cell holder and gates C, D and E provide for easy draining of all the pipes at each solution change, while limiting the occurrence of air bubbles in the installation.

In the following table, an example of operating mode is described to use the installation shown in FIG. 2.

TABLE

| | | Gates (O = Open; C = Closed) | | | | |
|---|---|---|---|---|---|---|
| Phase | Description | A | B | C | D | E |
| Injection of first solution | | | | | | |
| Phase 1 | Placing assembly in a vacuum | O | C | O | O | C |
| Phase 2 | Filling the hydraulic circuit and cell | C | O | O | O | C |
| Phase 3 | Aspirating a quantity of solution into the syringe | C | O | O | O | C |
| Phase 4 | Circulating solution in the cell | C | O | C | C | O |
| Injection of following solution | | | | | | |
| Phase 5 | Change of solution (or change of bottle) | O | C | C | C | O |
| Phase 6 | Repeat of phases 3 and 4 | | | | | |

During phase 1 of this operating mode, the cell and pipe network assembly is placed in a vacuum and the solution of bottle 23 is de-gased by opening gates A, C and D and by closing gates B and E.

After this operation, phase 2 consists of filling the hydraulic circuit and the cell by closing gates A and E and by opening gates B, C and D.

During phase 3, a quantity of solution is aspirated into syringe 17, by activating the syringe, gates B, C and D being open and gates A and E being closed.

During the following phase 4, the solution is caused to circulate in the cell by pushing syringe 17 and by opening gates B and E, gates A, C and D being closed. It is then possible to measure the load loss in the cell by means of the pressure sensor 19. To conduct a new analysis or to rinse the assembly, bottle 23 can be changed, gates A and E being open, and gates B, C and D being closed. It is then possible to conduct a new analysis following the operating mode of phases 3 and 4 as previously.

In this cell, the active zone which corresponds to the confined flow zone 9 was treated so that its wall is able to fix an analyte or a ligand of the analyte to be detected.

The examples given below illustrate the treatments used to fix a ligand made of capture antibodies onto the silicon wall of the active zone of the cell, and the use of this cell to determine an analyte made up of other antibodies able to be immobilized by the capture antibodies.

EXAMPLE 1

Functionalization of the Wall of the Confined Flow Zone

This operation can be conducted on substrates 5 and 7 before their assembly to form the cell.

For this purpose, the structures are boiled in pure water for 2 hours, and are then dried in an inert nitrogen atmosphere or in a vacuum. The structures are made up of the substrate-supports 5 and 7, the surfaces not requiring treatment may be masked. The structures obtained are placed in a flask containing a silane solution such as a 2% solution of methyl-n-octadecyldiethoxysilane in toluene and they are held in this solution under reflux for 1 hour. In this way an inner silanized surface is obtained in particular on the confined flow zone 9. It is also possible to conduct silanization with ultrasound for 1 hour. After this operation, the structures are rinsed several times in acetone, then dried at 120° C. After silanization, any masks that may have been used can be removed.

This silanization step makes it possible to modify the surface properties of the silica by generating a hydrophobic surface allowing antibody adsorption.

Figure 3:
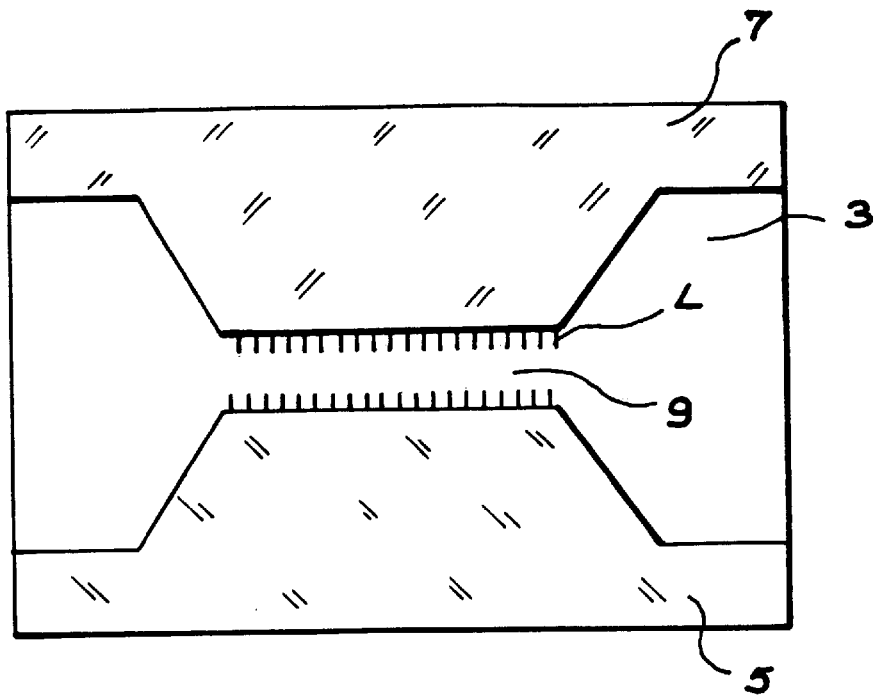
FIG. 3 is a vertical section view of the active zone of the cell in FIG. 1 containing a ligand coating.
Figure 6:
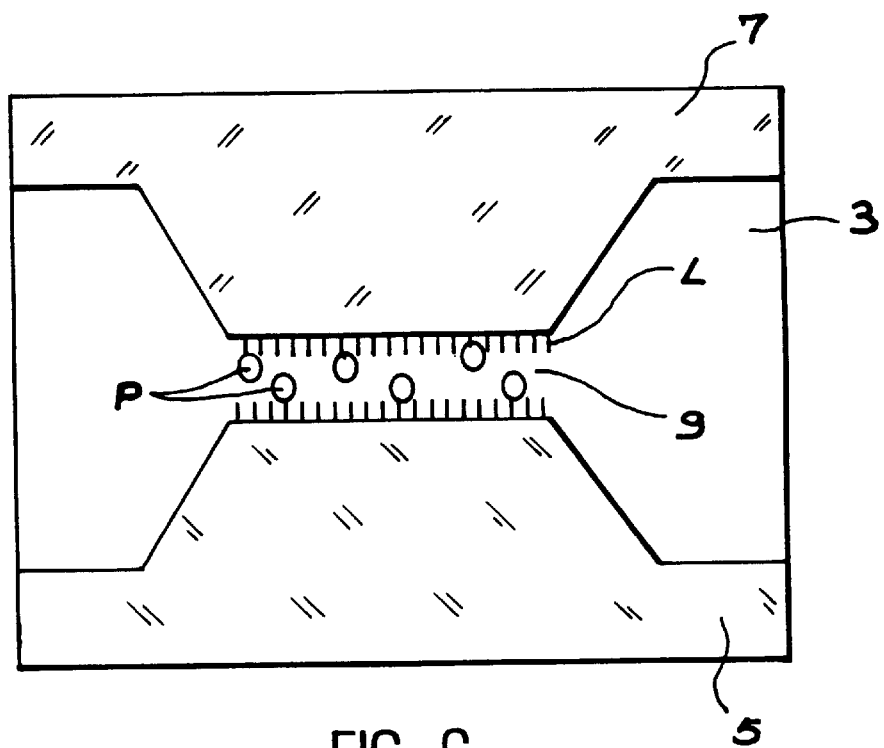
FIG. 6 is a vertical section view of the active zone of the cell in FIG. 1, after immobilization of the analyte on the ligand.

If a mask is used, treated surfaces in accordance with FIGS. 3 and 6 are obtained. If no masks are used these treated surfaces then have the structure shown in FIGS. 8 and 9.

The joining of substrates 5 and 7 to form the conduit is made either after silanization, in particular to allow removal of any masks before joining, or before silanization.

EXAMPLE 2

Fixing a Ligand Onto the Wall of the Confined Flow Zone

In this example, the ligand is made up of capture antibodies.

To carry out this fixing operation, the cell and piping assembly is first rinsed with water and then ethanol dried. To bottle 23 is added an antiferritin monoclonal mouse antibody to the proportion of 40 mg/ml in PBS buffer (50 mM phosphate, 0.15 M NaCl, pH 7.4), then the entire installation is placed in a vacuum by opening gates A, C and D and by closing gates B and E. Atmospheric pressure is then suddenly restored by opening gates B, C and D and by closing gate A, gate E remaining closed, such as to ensure instant filling of the cell, in particular at active zone 9, with no bubble formation. The absence of bubbles is confirmed by infrared microscopy which can visualize the inside of zone 9. The antibody solution is pumped from bottle 23 using syringe 17 and it is then injected into the cell at a controlled flow rate using syringe plunger 17, gates A, C and D being closed and gates B and E being open. The excess antibody solution in the syringe is removed, and the assembly is rinsed with PBS rinsing buffer containing 0.5% Tween 20 after changing bottle 23 and by repeating phases 3 and 4 of the table.

FIG. 3 shows a vertical section view of active zone 9 of the circulation cell coated with ligand L made up of capture antibodies (in the particular case when a mask is used).

The fixing of ligand L is confirmed by an enzyme-immunology test (ELISA) using antimouse goat antibodies labelled with an enzyme: alkaline phosphatase (AKP). This enzyme reacts with its specific substrate, p-nitrophenylphosphate (pNPP) to give a stained product determined by spectrophotometry at 405 nanometres.

Figure 4:
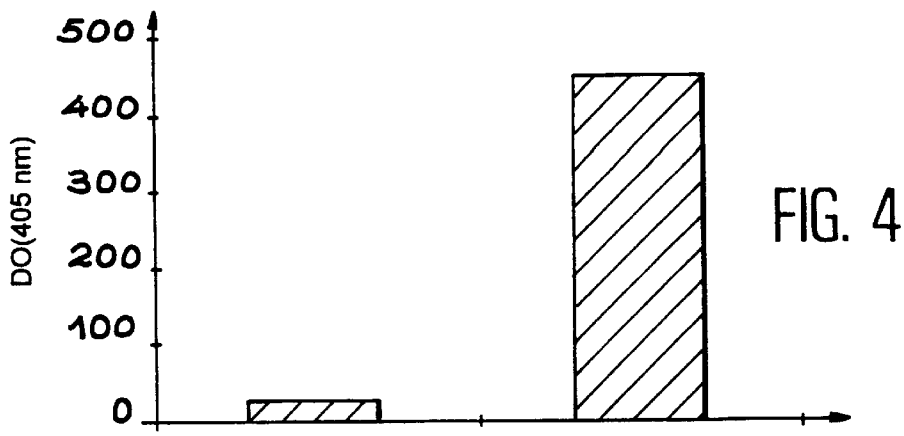
FIG. 4 is a diagram illustrating the fixing of a capture antibody on the active zone of the cell in FIG. 1.

FIG. 4 shows the optical density OD at 405 nm obtained with the wall coated with capture antibodies (positive control). By way of comparison, this figure also shows the optic density obtained with a silanized wall but which has not undergone the adsorption step of capture antibodies.

This figure confirms the presence of capture antibodies in active zone 9 of the cell.

It is also possible to determine the presence of these capture antibodies with the method of the invention by comparing the load loss obtained in the cell treated with capture antibodies with the load loss obtained in the cell before treatment with the capture antibody solution.

According to theory, the load loss $\Delta P$ during the flow of a fluid having a dynamic viscosity u in the confined flow zone 9 of height h, for a flow rate Q over a width b and a length l, is defined by the formula:

$$\Delta P = \frac{6\mu l}{bh^3} Q$$

Therefore, for a cell in which:

$h=4$ μm $b=l=2$ mm and a fluid whose viscosity $\mu$ is $10^{-3}$ kg/ms at 20° C., the result is $\Delta P$ (in $10^{-1}$ MPa)=16Q (in μl/min).

The linearity of this relationship between $\Delta P$ and Q in the cell of the invention was verified by causing the PBS-Tween buffer to circulate in the cell at different flow rates.

Figure 5:
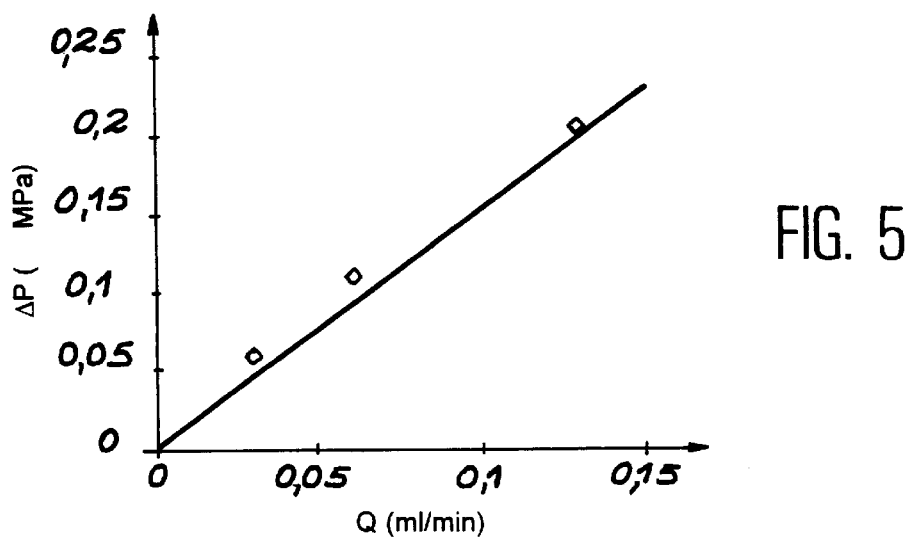
FIG. 5 is a diagram showing the variation in load loss ΔP in a conduit (in MPa) in relation to flow rate Q in the conduit (in ml/min).

FIG. 5 shows the variations in load loss $\Delta P$ (in MPa) in the cell in relation to flow rate Q (in ml/min) and confirms the linearity of this relationship.

EXAMPLE 3

Determination of An Analyte Made Up of Antimouse Goat Antibodies

In this example, the cell prepared in the preceding example is used, that is to say whose wall in active zone 9 is coated with a ligand L made up of capture antibodies, antiferritin monoclonal mouse antibodies.

For this determination, first an analyte-support conjugate is formed to increase the size of the analyte. For this purpose, latex particles 1 μm in diameter are used as a support and they are caused to react with the antimouse goat antibodies to form the analyte-support conjugate in PBS-Tween at a dilution of 1:100. The antimouse polystyrene-antibody latex particles are marketed by Polyscience Inc. USA under reference 17694.

The solution of latex particles functionalized with the antibodies is placed in bottle 23, and it is then injected into the cell as previously described for the capture antibody and washing buffer solution, at a flow rate of 0.3 ml/min.

In this way the structure shown in FIG. 6 is obtained. In this figure it can be seen that ligands L fixed on the wall of the active zone 9 of the cell are bound to the functionalized latex particles P (analyte-support conjugate), which partially obstruct the active zone 9 of the cell. The PBS buffer containing Tween 20 is then circulated in the cell at a flow rate of 0.3 ml/min and the load loss is measured by means of pressure sensor 19.

A value of 0.16 MPa is obtained, whereas for the negative control, that is to say the cell containing no ligand in its active zone, after injection of the solution of functionalized latex particles, the load loss is 0.03 MPa. This is accounted for by the fact that it is impossible to fix the latex particle/antimouse antibody conjugate on the wall of the active zone of the cell which does not contain the ligand formed by the capture antibodies.

Figure 7:
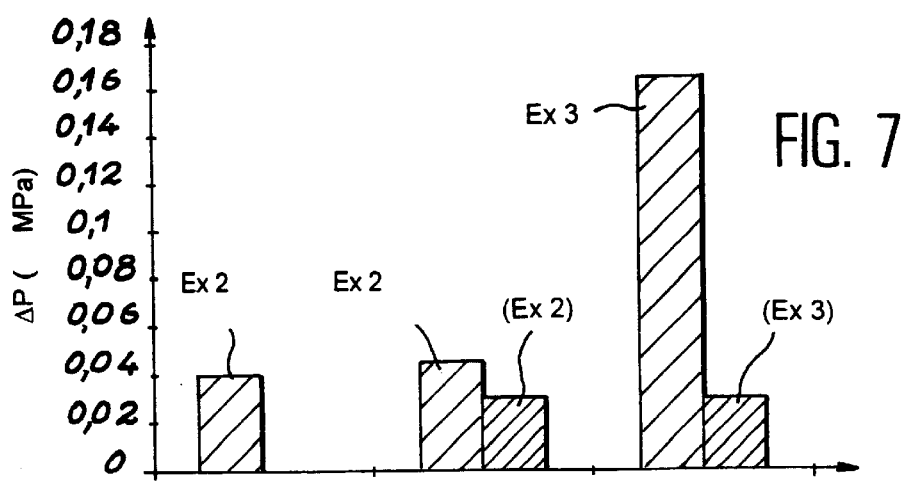
FIG. 7 is a diagram illustrating the variation in load loss ΔP (in MPa) in the active zone of the cell in relation to the fixed substances.

FIG. 7 shows the load losses of examples 2 (steps 1 and 2) and 3, and those of negative controls (no capture antibodies) in these two examples.

Step 1 relates to the load loss measured upstream from the cell during the injection of the antibodies. Step 2 corresponds to the measurement made with the PBS/Tween 20 washing solution after fixing the antibodies (flow rate of 0.03 ml/min). In example 3, the measurement is made with PBS-Tween 20 at a flow rate of 0.03 ml/min.

In the case shown in example 2 (steps 1 and 2) a slight increase is noted in the load loss due to the fixing of the capture antibodies. In the case shown in example 3, the increase in load loss is substantial. Also, according to the results of steps 1 and 2, it is noted that there is no increase in load loss when the solution is changed.

The finding is therefore made that the specific immobilization of the antibody-latex particle conjugates inside the circulating cell causes a decrease in the height of the active zone 9, which leads to an increase in load loss at constant flow rate.

In respect of the negative control in example 3, no variation in load loss is observed during the rinsing step of example 3. The latex particles have not modified the height of active zone 9 since they are not withheld in this active zone.

Figure 8:
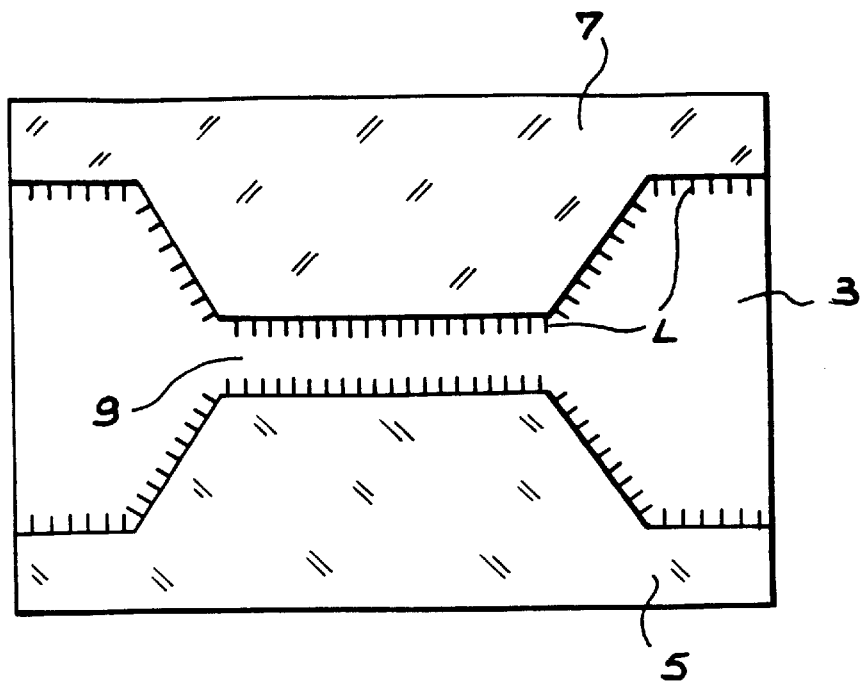
FIG. 8 shows a vertical section of the cell containing a coating of ligand L over the entire conduit.
Figure 9:
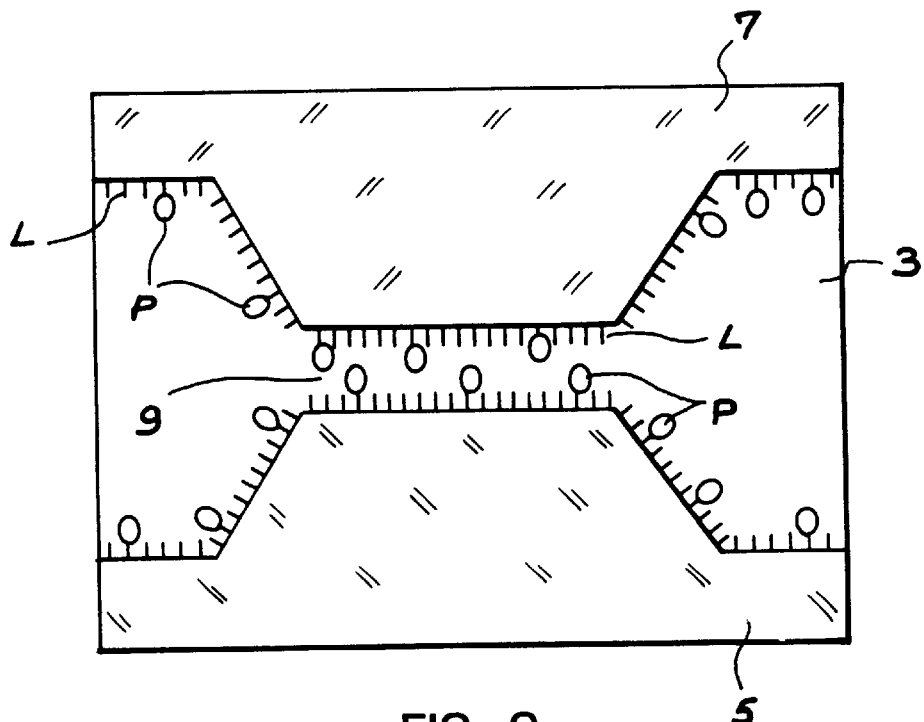
FIG. 9 is a vertical section view of the cell in FIG. 8, after immobilization of an analyte-support conjugate on ligand L.

FIGS. 8 and 9 illustrate cells in which the entire surface of circulation conduit 3 is coated with ligand L (FIG. 8), then with particles P of the analyte-support conjugate (FIG. 9). This relates to the case when all the inner surface of the conduit is functionalized as in example 1, without using a mask, and in which it is subsequently proceeded with fixing the ligand as in example 2, then with determining the analyte as in example 3.

Therefore, particles P are found in conduit 3 and confined zone 9. This presence cannot have any influence on load loss to be measured and forms a preferred embodiment of the invention since it is much simpler to implement.

CITED REFERENCES

[1]: FR-A-2 758 884
[2]: US-A-4 964 847
[3]: FR-A-2 727 648.

What is claimed is:

1. A method for determining the presence of an analyte in a solution, comprising the following steps:
   a) determining a system load loss of a conduit having a reduced cross section over all or part of it, as a function of fluid pressure and volumetric flow rate for a fluid circulating in said conduit,
   b) immobilizing said analyte on the inner surface of the reduced cross section of said conduit and determining a resulting load loss of the fluid circulating in the conduit,
   c) determining the variation in load loss of the fluid circulating in the conduit, due to the analyte which has been immobilized on the inner surface of the reduced cross section of said conduit during step b) as compared to the system load loss of step a), and
   d) correlating said variation in load loss to a standard to determine the presence of the analyte in the solution wherein, load loss is determined by measuring the pressure at constant flow rate or the flow rate at constant pressure between two points located either side of the reduced cross section of the conduit.

2. Method according to claim 1, in which step b) is conducted by contacting the solution with the inner surface of the conduit, or by circulating the solution in the conduit.

3. Method according to claim 1, in which the variation in load loss is determined by measuring the difference in pressure at constant flow rate.

4. Method according to claim 1, in which said fluid is all or part of the solution.

5. Method according to claim 1, in which said fluid is a different liquid than the solution.

6. Method according to claim 1 in which, prior to step b), the wall of the reduced cross section is coated over all or part with at least one ligand for interacting with the analyte.

7. Method according to claim 6, in which the presence of the ligand coating is detected by determining a variation in the system load loss through measuring the difference in pressure at constant flow rate or the difference in flow rate at constant pressure between two points located either side of the reduced cross section of the conduit, of a fluid circulating in the conduit, before and after conducting the ligand coating.

8. Method according to claim 1, which also comprises a physical or chemical reaction of the analyte with a support-material to form an analyte-support conjugate of greater size than that of the analyte, said reaction occurring either when said analyte is free in the solution, before step b), or when the analyte is already immobilized either directly or indirectly to the inner wall of the reduced section of the conduit after step b) to form an analyte-support conjugate.

9. Method according to claim 8, in which the support-material contains a ligand for forming a complex with the analyte.

10. Method according to claim 8, in which the support-material is made up of latex particles functionalized by a ligand specific to the analyte.

11. Method according to claim 1, which further comprises at least one washing step of the conduit between steps b) and c).

12. Method according to claim 6, in which the smallest dimension $T_c$ of the reduced cross section of the conduit is such that:

$$T_c/3 < T_A \text{ or } e < T_C$$

where $T_A$ represents the size of the immobilized analyte or in the form of an analyte-support conjugate, or e represents the thickness of the ligand.

13. A method for determining the presence of an analyte in a solution comprising the following steps:
   a) preparing a circulating cell including a conduit having a reduced cross section over all or part of it and having an active zone which interacts with said analyte,
   b) determining a first load loss of a fluid flowing through said circulating cell measured as a function of pressure and volumetric flow rate between an inlet and an outlet portion of said cell,
   c) immobilizing said analyte to the active zone,
   d) determining a second load loss of the fluid flowing through said circulating cell as in step b)
   e) correlating an analyte value as a function of the variation in the second load loss to the first load loss.

14. Method according to claim 13, wherein in step a) the active zone is a ligand immobilized on the wall of the circulating cell and having a functional group to interact with said analyte.

15. Method according to claim 13, in which said fluid is all or part of the solution.

16. Method according to claim 13, in which said fluid is a different liquid to the solution.

17. Method according to claim 14, in which the smallest dimension $T_C$ of the reduced cross section part of the conduit is such that:

$$T_c/3 < T_A \text{ or } e < T_C$$

in which $T_A$ represents the size of the immobilized analyte or in the form of an analyte-support conjugate, or e represents the thickness of the ligand.

* * * * *